(12) United States Patent
Anderson

(10) Patent No.: US 9,924,939 B1
(45) Date of Patent: Mar. 27, 2018

(54) SELF-CINCHING SUTURE CONSTRUCT APPARATUS

(71) Applicant: Christian N. Anderson, Nashville, TN (US)

(72) Inventor: Christian N. Anderson, Nashville, TN (US)

( * ) Notice: Subject to any disclaimer, the term of this patent is extended or adjusted under 35 U.S.C. 154(b) by 0 days.

(21) Appl. No.: 15/783,498

(22) Filed: Oct. 13, 2017

Related U.S. Application Data

(63) Continuation-in-part of application No. 15/643,173, filed on Jul. 6, 2017.

(51) Int. Cl.
    *A61B 17/04* (2006.01)
    *A61B 17/06* (2006.01)

(52) U.S. Cl.
    CPC .... *A61B 17/0487* (2013.01); *A61B 17/06166* (2013.01); *A61B 2017/0496* (2013.01)

(58) Field of Classification Search
    CPC ........ A61B 17/0487; A61B 2017/0496; A61B 17/06166; A61B 2017/06185
    See application file for complete search history.

(56) References Cited

U.S. PATENT DOCUMENTS

| 1,306,369 A | 6/1919 | Bell |
| 3,409,014 A | 11/1968 | Shannon |
| 4,291,698 A | 9/1981 | Fuchs et al. |
| 4,823,794 A | 4/1989 | Pierce |
| 4,896,366 A | 1/1990 | Oxman |
| D359,229 S | 6/1995 | Jules |

(Continued)

FOREIGN PATENT DOCUMENTS

| EP | 2455002 A1 | 5/2012 |
| EP | 2462876 A2 | 6/2012 |

(Continued)

OTHER PUBLICATIONS

Arthrex; www.arthrex.com; Arthroscopic Stabilization of Acute Acromioclavicular Joint Dislocation Using the TightRope System; Surgical Technique; 2010; six pages.

(Continued)

*Primary Examiner* — Jonathan Miles
*Assistant Examiner* — Wade Miles
(74) *Attorney, Agent, or Firm* — Waller Lansden Dortch & Davis, LLP; Matthew C. Cox

(57) ABSTRACT

A knotless self-cinching suture construct device includes a shuttling suture, a continuous loop and a self-cinching suture member. The shuttling suture is configured for insertion into a passage hole in injured soft tissue, such as a torn or damaged meniscus in the knee. The shuttling suture and continuous loop are passed entirely through the passage hole in the tissue, and the self-cinching suture member is inserted through the continuous loop to form a hitch using the continuous loop around the tissue. The self-cinching suture member is then pulled tight, allowing a first strand to slide through both the hitched continuous loop and a self-cinching sleeve on the suture member. When tension is applied, the sleeve tightens around the strand much like a finger trap, preventing inadvertent release of the applied suture tension. The suture construct is configured for use through a transosseous tunnel with a suture button in some embodiments.

20 Claims, 16 Drawing Sheets

(56) References Cited

U.S. PATENT DOCUMENTS

| | | | |
|---|---|---|---|
| 5,645,588 A | 7/1997 | Graf et al. | |
| 6,066,160 A | 5/2000 | Colvin et al. | |
| 6,660,023 B2 | 12/2003 | McDevitt et al. | |
| 6,716,234 B2 | 4/2004 | Grafton et al. | |
| 7,217,279 B2 | 5/2007 | Reese | |
| 7,390,332 B2 * | 6/2008 | Selvitelli | A61B 17/0401 606/144 |
| D576,867 S | 9/2008 | Kretz | |
| 7,594,922 B1 | 9/2009 | Goble et al. | |
| 7,601,165 B2 | 10/2009 | Stone | |
| 7,862,584 B2 | 1/2011 | Lyons et al. | |
| 7,905,903 B2 * | 3/2011 | Stone | A61B 17/0401 606/232 |
| 8,109,968 B2 | 2/2012 | Ashley et al. | |
| 8,128,658 B2 | 3/2012 | Kaiser et al. | |
| 8,162,997 B2 | 4/2012 | Struhl | |
| 8,231,674 B2 | 7/2012 | Albertorio et al. | |
| 8,348,960 B2 | 1/2013 | Michel et al. | |
| 8,439,976 B2 | 5/2013 | Albertorio et al. | |
| 8,460,379 B2 | 6/2013 | Albertorio et al. | |
| 8,545,535 B2 | 10/2013 | Hirotsuka et al. | |
| 8,562,645 B2 | 10/2013 | Stone et al. | |
| 8,591,578 B2 | 11/2013 | Albertorio et al. | |
| 8,663,324 B2 | 3/2014 | Schmieding et al. | |
| 8,753,375 B2 | 6/2014 | Albertorio | |
| 8,821,541 B2 | 9/2014 | Dreyfuss et al. | |
| 8,936,621 B2 | 1/2015 | Denham et al. | |
| 9,107,653 B2 | 8/2015 | Sullivan | |
| 9,173,645 B2 * | 11/2015 | Overes | A61B 17/0057 |
| 9,179,907 B2 | 11/2015 | Elattrache et al. | |
| 9,345,471 B2 | 5/2016 | Sullivan | |
| 9,381,013 B2 * | 7/2016 | Norton | A61B 17/0401 |
| 9,451,953 B2 | 9/2016 | Sengun | |
| 9,510,819 B2 | 12/2016 | Stone et al. | |
| 2003/0236555 A1 | 12/2003 | Thornes | |
| 2005/0197662 A1 | 9/2005 | Clark et al. | |
| 2007/0083236 A1 * | 4/2007 | Sikora | A61B 17/0401 606/232 |
| 2007/0239209 A1 | 10/2007 | Fallman | |
| 2008/0255613 A1 | 10/2008 | Kaiser et al. | |
| 2009/0105754 A1 | 4/2009 | Sethi | |
| 2010/0256677 A1 | 10/2010 | Albertorio et al. | |
| 2010/0268273 A1 | 10/2010 | Albertorio et al. | |
| 2012/0053630 A1 | 3/2012 | Denham et al. | |
| 2012/0150203 A1 | 6/2012 | Brady et al. | |
| 2013/0023928 A1 | 1/2013 | Dreyfuss | |
| 2013/0165972 A1 | 6/2013 | Sullivan | |
| 2013/0168478 A1 | 7/2013 | Holman | |
| 2013/0190819 A1 | 7/2013 | Norton | |
| 2013/0345749 A1 | 12/2013 | Sullivan et al. | |
| 2013/0345750 A1 | 12/2013 | Sullivan | |
| 2014/0031864 A1 | 1/2014 | Jafari et al. | |
| 2014/0114352 A1 | 4/2014 | Allen | |
| 2014/0250636 A1 | 9/2014 | Vantrease | |
| 2014/0277121 A1 | 9/2014 | Pilgeram et al. | |

FOREIGN PATENT DOCUMENTS

| | | |
|---|---|---|
| EP | 2572648 A1 | 3/2013 |
| EP | 2581047 A1 | 4/2013 |
| EP | 2724673 A1 | 4/2014 |
| EP | 2777513 A1 | 9/2014 |
| EP | 2263608 B1 | 9/2016 |

OTHER PUBLICATIONS

Rosenberg, Thomas D. MD; Smith & Nephew, Inc., Endoscopy Division, ACL Reconstruction with the ACUFEX Director Drill Guide and EnboButton CL Fixation System; Knee Series, Technique Guide, ; 12 pages.

Stryker; www.stryker.com; Joint Preservation; VersiTomic G-Lok, 2011; four pages.

DePuy Synthes Mitek Sports Medicine, Companies of Johnson RIGIDLOOP Adjustable Cortical System Quick Surgical Technique Guide for Soft Tissue ACL Reconstruction; 2014, two pages.

Smith&Newphew; ULTRABUTTON Adjustable Fixation Device; 2016; PN: 71577 Rev. A Feb. 2016; 29 pages.

* cited by examiner

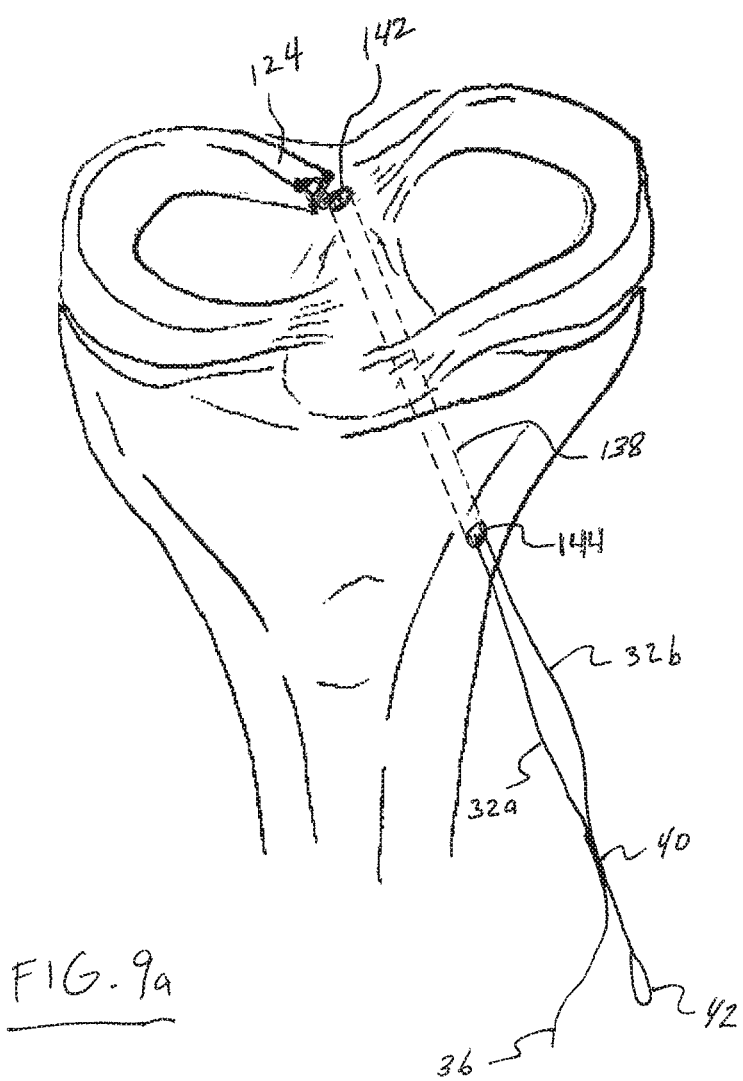

SELF-CINCHING SUTURE CONSTRUCT APPARATUS

CROSS-REFERENCE TO RELATED APPLICATION

This application claims priority to and benefit of copending U.S. patent application Ser. No. 15/643,173 filed Jul. 6, 2017 entitled Suture Button Construct for Surgical Procedures, all of which is hereby incorporated by reference in its entirety.

BACKGROUND

The present invention relates generally to surgical devices and methods and more particularly to suture devices and methods to secure damaged soft tissue structure.

Various types of sutures, suture fixation devices and associated methods are known in the art for securing a suture in a desired position and/or at a desired tension during and after surgical procedures. In many surgical procedures, a transosseous hole is drilled through a portion of bone, forming a rigid tunnel for passing a surgical instrument or a suture. The drilled tunnel includes a proximal opening adjacent a tissue repair site where a procedure for the repair of tissue is generally performed, such as but not limited to a procedure to repair a meniscus root tear in a knee. The drilled tunnel generally also includes a distal opening at a location remote from the repair site.

During surgical procedures, one or more sutures are attached to the tissue to be repaired. A free end of the suture is inserted through an opening of the drilled tunnel near the tissue and passed through the tunnel to a tunnel exit. The suture then exits the tunnel and is tensioned to manipulate the damaged tissue into a desired anatomical position. The free end of the suture extending out of the tunnel exit must be pulled tight to maintain tension on the tissue following the operation. After tension is applied, the held in place using an anchor or suture button to maintain the desired tension.

Numerous types of sutures, suture buttons and suture anchors are known in the art for tying off sutures on the distal end of transosseous tunnels for maintaining tension. However, such conventional sutures, suture buttons and suture anchors are often inadequate and may lead to unintentional release of the applied tension on the suture over time. This release of tension may cause the tissue to heal improperly, leading to discomfort and pain at the joint and potentially requiring additional operations to reapply the necessary tension.

For example, with regard to conventional sutures, such devices for meniscus root repair and other operations on the knee have a disadvantage of requiring one or more knots on the outside of the drill tunnel opening to secure the soft tissue in place. The knots may rub against the soft tissue, causing discomfort or irritation. Likewise, knots positioned near the drill tunnel exit also cause discomfort and irritation.

Additionally, when the suture is pulled tight to reduce the soft tissue to its desired anatomical position, the suture has a tendency to allow the button to move slightly away from the bone. The button may also inadvertently move away from the bone when a knot is tied in the suture at the button site. Any gap between the button and the bone may result in a loss of tension in the suture.

Further, knotted suture constructs for meniscus root repair may slip or loosen over time as knots work loose. Such loosening of knotted suture constructs may cause damage to the tissue, improper healing and further injury.

What is needed, then are improvements in suture construct devices and methods for surgical procedures.

BRIEF SUMMARY

The present invention generally provides a suture construct device and associated methods for providing traction to torn or damaged tissue.

The suture construct device includes a shuttling suture, a continuous loop, and a self-cinching suture member linked together. The shuttling suture is configured for insertion through a passage hole in the tissue. The shuttling suture and continuous loop are pulled through the passage hole, and the self-cinching suture construct is passed through the continuous loop, forming a hitch in the continuous loop around the tissue. When the self-cinching suture member is pulled tight, a strand of the self-cinching suture passes through a self-cinching sleeve. As tension is increased, the sleeve creates a clamping effect on the self-cinching suture strand passing through the sleeve, preventing the suture from inadvertently loosening.

Another object of the present disclosure provides a suture construct device that can be tightened without the use of a knot.

A further object of the present disclosure is to provide a suture construct device with a shuttling suture that can be removed after passage of the continuous loop through tissue.

Yet another object of the present disclosure is to provide a suture construct device with a tapered shuttling suture that dilates the passage hole to allow for passage of the continuous loop.

Another object of the present disclosure is to provide a suture construct device with a shuttling suture having a dilation member to widen the passage hole to allow for passage of the continuous loop.

Another object of the present disclosure is to provide a suture construct device configured to form a girth hitch on torn tissue to prevent suture material from slicing through the tissue.

Yet another object of the present disclosure is to provide a suture construct device configured for use with a variety of surgical buttons for transosseous tunnel suture fixation.

A further object of the present disclosure is to provide a suture construct device for use with transosseous tunnel suture fixation wherein a self-cinching sleeve is housed inside the transosseous tunnel when the suture is tensioned.

Numerous other objects, features and advantages of the present invention will be readily apparent to those skilled in the art upon a reading of the following disclosure when taken in conjunction with the accompanying drawings.

BRIEF DESCRIPTION OF THE DRAWINGS

FIG. 9a illustrates a perspective view of an embodiment of a self-cinching suture construct positioned for installation on a torn meniscal root in a knee.

DETAILED DESCRIPTION

Figure 1:
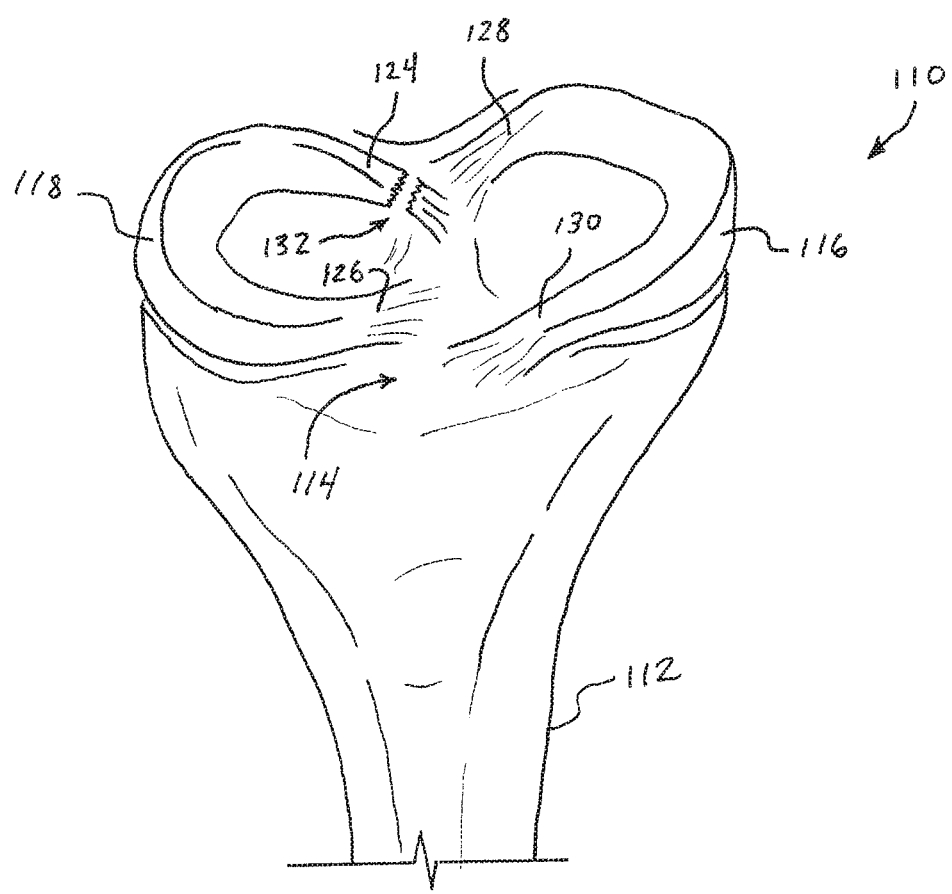
FIG. 1 illustrates a perspective view of an embodiment of a portion of knee including a meniscal root tissue injury.

Referring now to the drawings, various views of embodiments of a self-cinching suture construct apparatus and associated methods are illustrated. In the drawings, not all reference numbers are included in each drawing, for the sake of clarity. In addition, positional terms such as "upper," "lower," "side," "top," "bottom," "vertical," "horizontal" etc. refer to the apparatus when in the orientation shown in the drawings or similar orientations. A person of skill in the art will recognize that the apparatus can assume different orientations when in use.

The present disclosure provides a self-cinching suture construct for use in surgical procedures, including but not limited to operations on the knee. As shown in FIG. 1, an embodiment of a knee 110 showing the upper end of a tibia 112 including a medial meniscus 116 and a lateral meniscus 118. The medial meniscus 116 includes a posterior root 128 and an anterior root 130. The lateral meniscus 118 includes a posterior root 124 and an anterior root 126. Each root is attached to the tibia at local tissue attachment sites along the tibial plateau 114. Various types of injuries may lead to one or more root tears or injuries in the lateral or medial meniscus. An example of a root tear 132 on the lateral posterior root 124 is shown in FIG. 1.

Although various figures refer to an exemplary lateral posterior root tear injury, the devices and methods of the present disclosure are applicable to many different types of injuries, including but not limited to tears and injuries in the anterior lateral meniscus and posterior lateral meniscus as well as the anterior medial meniscus and posterior medial meniscus. The examples demonstrating application to a lateral posterior meniscus root tear are offered only as a non-limiting example.

Figure 2:
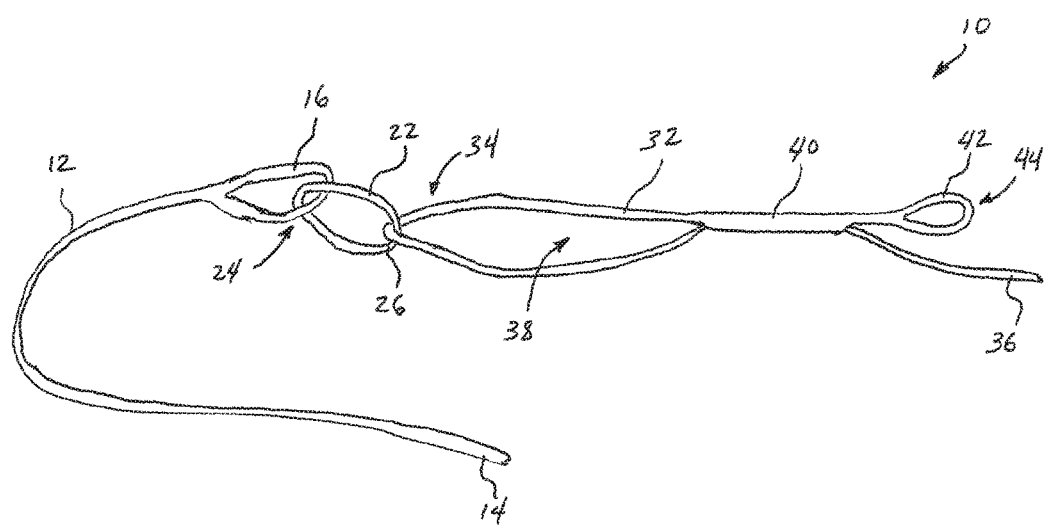
FIG. 2 illustrates a perspective view of an embodiment of a self-cinching suture construct apparatus in accordance with the present disclosure.

The present disclosure provides a self-cinching, knotless suture construct device for repairing a meniscus root tear in a knee. As shown in FIG. 2, an embodiment of a suture construct device 10 is illustrated. The suture material may include any suitable suture material known in the art. Device 10 includes a shuttling suture 12 forming a leading shuttling suture free end 14. Shuttling suture 12 includes a shuttling suture fixed loop 16 at its trailing end opposite the leading shuttling suture free end 14. Leading shuttling suture free end 14 on shuttling suture 12 is positioned for initial insertion into the injured tissue for beginning a suture attachment procedure.

The embodiment of a suture construct device 10 shown in FIG. 2 is not drawn to scale, and the relative lengths, shapes and diameters of the various suture construct features may vary considerable based on the desired application.

Next to the shuttling suture 12, a ring-shaped continuous loop 22 is attached to the shuttling suture fixed loop 16. Continuous loop 22 forms a continuous ring passing through the opening formed by the shuttling suture fixed loop 16. Continuous loop 22 includes a continuous loop leading edge 24 and a continuous loop trailing edge 26. Continuous loop leading edge 24 provides the engagement location between continuous loop 22 and shuttling suture fixed loop 16. Continuous loop 22 includes any suitable suture material known in the art. Continuous loop 22 may be formed by splicing or connecting tag ends of a strand of suture material together. Similarly, shuttling suture fixed loop 16 may be formed by splicing or connecting a tag end of shuttling suture 12 back onto itself to form a fixed loop. Alternatively, continuous loop 22 or shuttling suture fixed loop 16 may be integrally formed on each respective suture member in a molding process.

A third, self-cinching suture member 32 is disposed on the suture construct device 10 joining continuous loop 22. The self-cinching suture member 32, or knotless repair suture 32, includes a self-cinching suture leading end 34 positioned on the forward end toward the continuous loop 22. The self-cinching suture leading end 34 passes through the ring-shaped opening formed by continuous loop 22. Self-cinching suture member 32 is configured to pass through a transosseous tunnel in a patient's bone during a meniscal root tear repair procedure in some embodiments.

Referring further to FIG. 2, a sleeve 40 is disposed on the self-cinching suture member 32. In some embodiments, self-cinching suture member 32 is constructed of a suture material having an annular cross-sectional profile, forming an elongated tube. Such suture material may include braided or non-braided suture material. In some embodiments, sleeve 40 is defined within the interior hollow body of the suture material.

For example, a self-cinching suture member free end 36 may be passed through a sleeve segment 40 of the self-cinching suture member body, as shown in FIG. 2. The segment of the suture body surrounding the passed-through portion forms a sleeve 40 around the suture strand of the self-cinching suture member free end 36.

Thus, a portion of the suture strand between self-cinching suture member free end 36 and the self-cinching suture leading end 34 may slide through sleeve 40. As tension is applied to the suture member, the sleeve 40 may tighten around the suture strand passing through sleeve 40, thereby securing or locking the suture strand in place relative to the sleeve. Sleeve 40 provides a clamping effect against the strand of suture material passing through the sleeve. The clamping effect prevents the strand from inadvertently loosening during use. More specifically, during use, when self-cinching suture member 32 is pulled tight, sleeve 40 restricts axial translation of self-cinching suture member free end 36. As such, the suture member may be referred to as a "self-cinching" or "knotless" suture construct.

Referring further to FIG. 2, another feature of self-cinching suture member 32 includes a retaining structure such as a self-cinching suture fixed loop 42 formed at the self-cinching suture trailing end 44. During a surgical procedure, a suture button or suture anchor may be secured to device 10 at the self-cinching suture fixed loop 42. The application of tension to self-cinching suture member free end 36 causes the self-cinching suture member 32 to slide through continuous loop 22 and to be generally drawn back toward the continuous loop 22. This motion effectively forms an adjustable loop 38 which closes as tension is applied.

Figure 3:
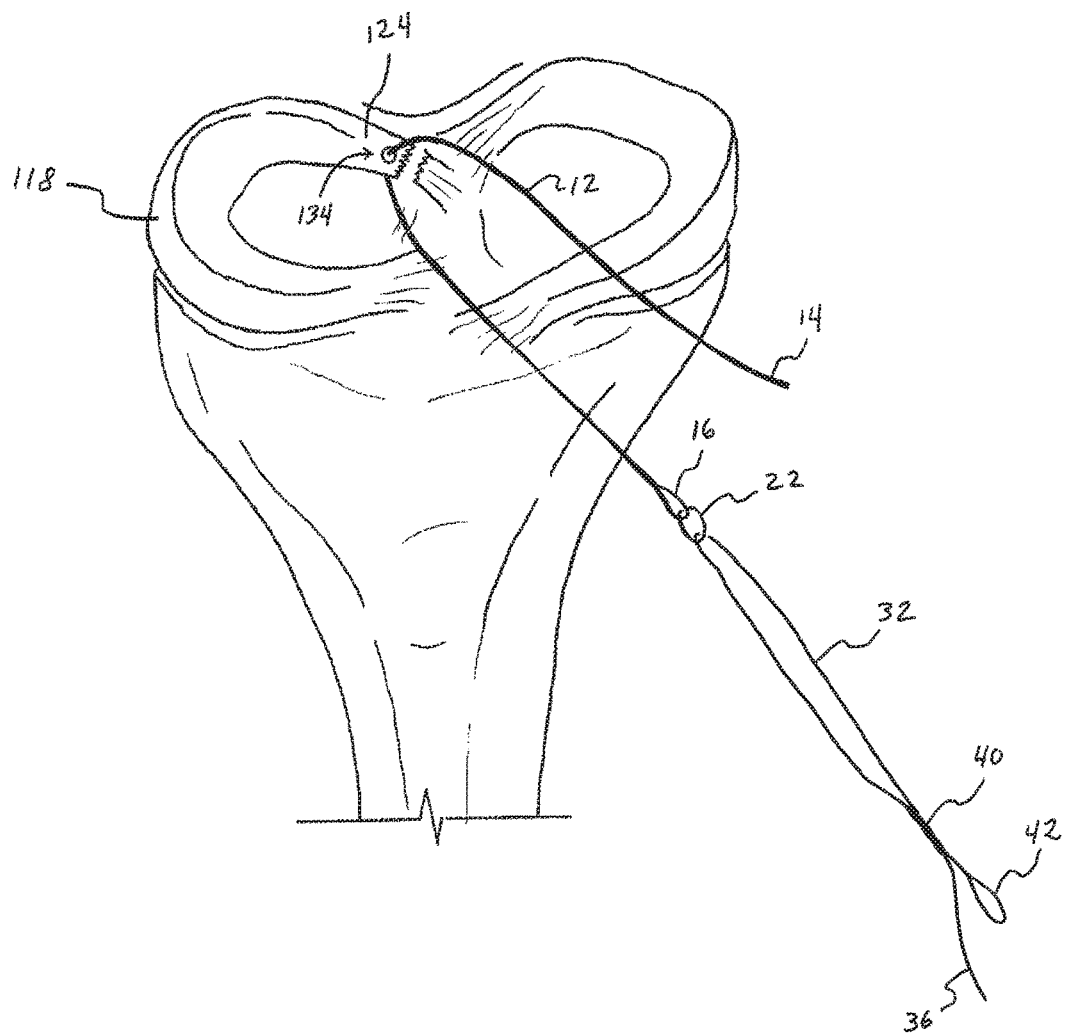
FIG. 3 illustrates a perspective view of an embodiment of a self-cinching suture construct positioned for installation on a torn meniscal root in a knee.

An example of a suture construct device 10 configured for meniscus root tear repair is shown in FIG. 3. The device includes three main components: a shuttling suture 12, a continuous loop 22, and a self-cinching suture member 32. The leading shuttling suture free end 14 is inserted through the damaged tissue of a meniscus root 124. The leading shuttling suture free end 14 may be inserted in the torn meniscal root 124 using any suitable instrument for passing a suture through tissue. As the leading shuttling suture free end 14 is passed through the torn meniscal root tissue, a passage hole 134 is formed, creating an opening in the soft tissue of the injured tissue through which the suture material of the shuttling suture 12 may slide.

Figure 10:
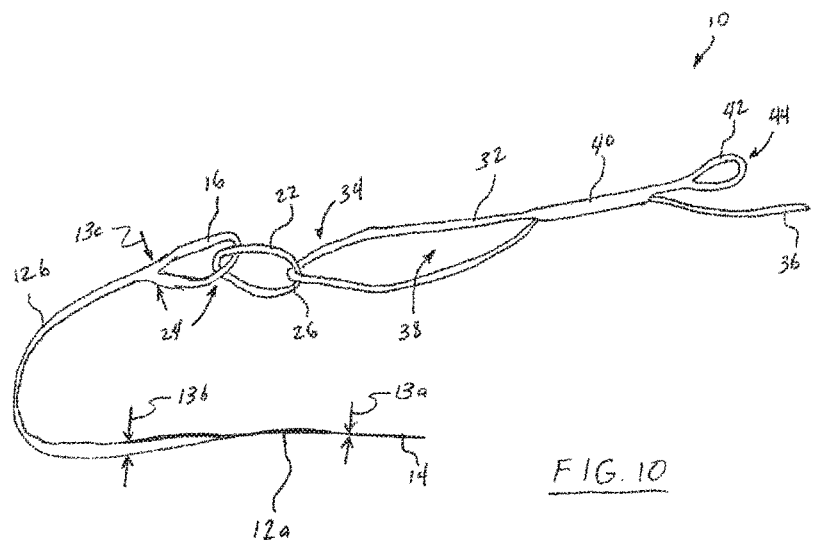
FIG. 10 illustrates a perspective view of an alternative embodiment of a self-cinching suture construct apparatus in accordance with the present disclosure.

In some applications, it is generally desirable that passage hole 134 be widened to accommodate smooth passage of both shuttling suture 14 and subsequent passage of continuous loop leading edge 24 on continuous loop 22. The meniscus tissue of meniscal root 124 may dilated to further open passage hole 134 by including a tapered region on shuttling suture 12. For example, as shown in FIG. 10, a shuttling suture 12 includes a first shuttling suture section 12a having a first shuttling suture diameter 13a, and a second shuttling suture section 12b having a second shuttling suture diameter 13b. In some embodiments, the second shuttling suture diameter 13b is greater than the first shuttling suture diameter 13a. This provides a tapered geometry on shuttling suture 12. Additionally, as seen in FIG. 10, shuttling suture fixed loop 16 includes a third shuttling suture diameter 13c adjacent second shuttling suture section 12b. The third shuttling suture diameter 13c is formed where the shuttling suture fixed loop 16 includes a double suture thickness forming the loop. The third shuttling suture diameter 13c is greater than second shuttling suture diameter 13b and is also greater than first shuttling suture diameter 13a in some embodiments.

Figure 4:
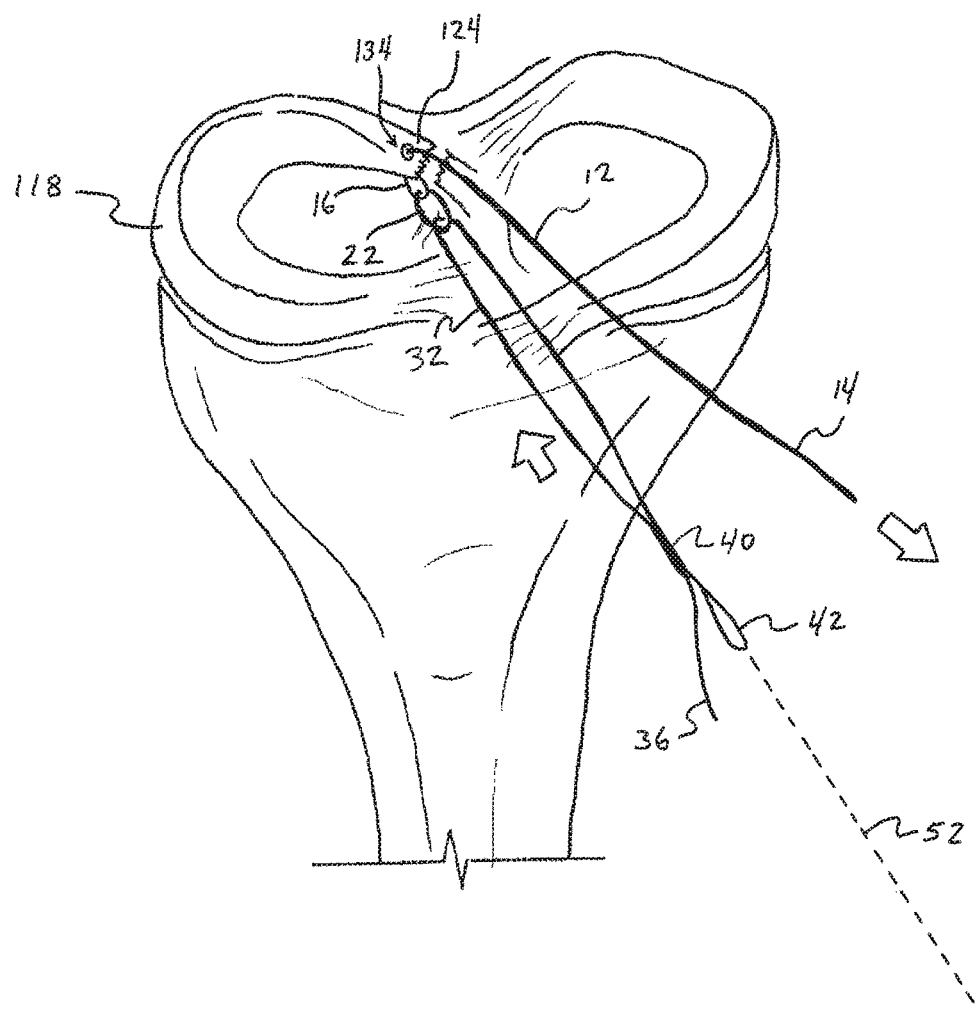
FIG. 4 illustrates a perspective view of an embodiment of a self-cinching suture construct positioned for installation on a torn meniscal root in a knee.

An example of the passage of shuttling suture 12 through passage hole 134 is shown in FIG. 4. During use, the leading shuttling suture free end 14 is passed through passage hole 134 and doubled back away from the tissue. The leading shuttling suture free end 14 is pulled away from the tissue, thereby drawing continuous loop 22 and self-cinching suture member 32 toward the passage hole 134. As the shuttling suture 12 is pulled through the passage hole 134, the passage hole 134 may be dilated further as the sections of shuttling suture 12 with increasing diameter are pulled through the passage hole 134.

Figure 11:
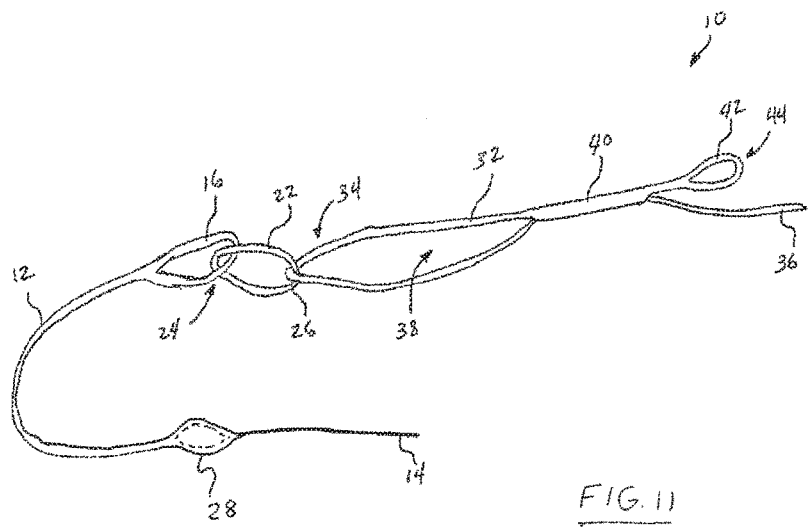
FIG. 11 illustrates a perspective view of an alternative embodiment of a self-cinching suture construct apparatus in accordance with the present disclosure.
Figure 12:
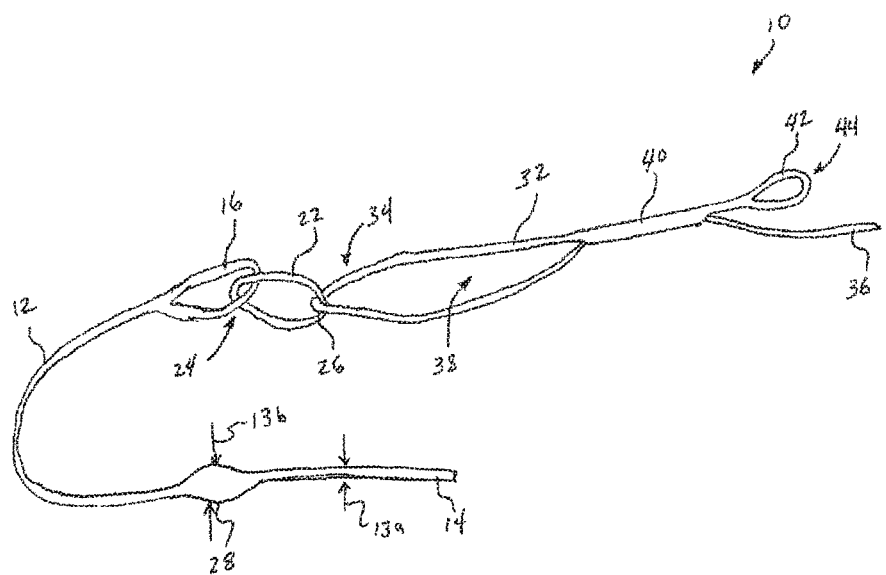
FIG. 12 illustrates a perspective view of an alternative embodiment of a knotless self-cinching suture construct apparatus in accordance with the present disclosure.

In additional embodiments, as seen in FIG. 11 and FIG. 12, a dilation member 28 may be positioned on shuttling suture 12. Dilation member 28 includes an increased diameter 13b as compared to the diameter 13a of shuttling suture 12. Dilation member 28 may include any suitable member, such as an integral region on shuttling suture 28 having an increased diameter 13b. Alternatively, dilation member 28 includes an oval-shaped bead or insert disposed on shuttling suture 12 positioned to enlarge the size of passage hole 134 when the dilation member 28 passes through the passage hole 134. This dilation of passage hole 134 better accommodates passage of continuous loop 22.

As shown in FIG. 10 and FIG. 11, in some embodiments, shuttling suture 12 includes a dilation member 28 and a tapered profile including a first shuttling suture section 12a and a second shuttling suture section 12b. As shown in FIG. 12, shuttling suture 12 includes a dilation member 28 positioned on a shuttling suture 12 having a uniform diameter.

Figure 13:
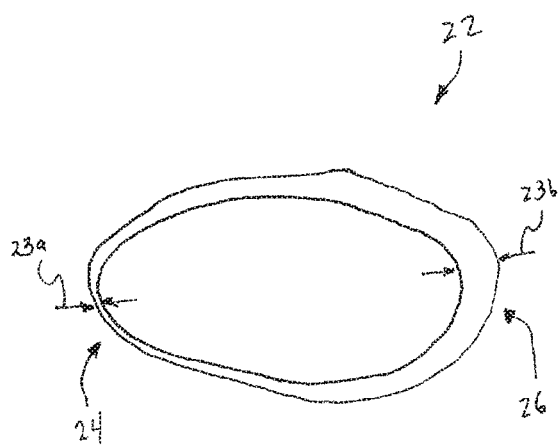
FIG. 13 illustrates a plan view of an embodiment of a tapered continuous loop in accordance with the present disclosure.

In alternative embodiments, the entry of continuous loop 22 into passage hole 134 may be improved by providing a tapered continuous loop 22, as shown in FIG. 13. Tapered continuous loop 22 includes a continuous loop leading edge 24 having a first continuous loop diameter 23a, and a continuous loop trailing edge 26 having a second continuous loop diameter 23b. In some embodiments, first continuous loop diameter 23a is less than second continuous loop diameter 23b. Thus, as the leading edge 24 of continuous loop 22 is pulled into passage hole 134, the smaller diameter section enters passage hole 134 first making entry easier.

Referring again to FIG. 4, a suture construct device 10 is positioned for insertion into a torn lateral posterior meniscus root 124 on a knee. The shuttling suture 12 is positioned through the passage hole 134, and the continuous loop 22 is advancing toward the passage hole 134. As the leading shuttling suture free end 14 is advanced further away from the tissue, slight tension may be maintained on the self-cinching suture member 32 by slightly pulling on self-cinching suture member fixed loop 42 and self-cinching suture member free end 36. In some embodiments, a tether 52 may be used to maintain tension on self-cinching suture member fixed loop 42 as the self-cinching suture member 32 advances toward the passage hole 134.

Figure 5:
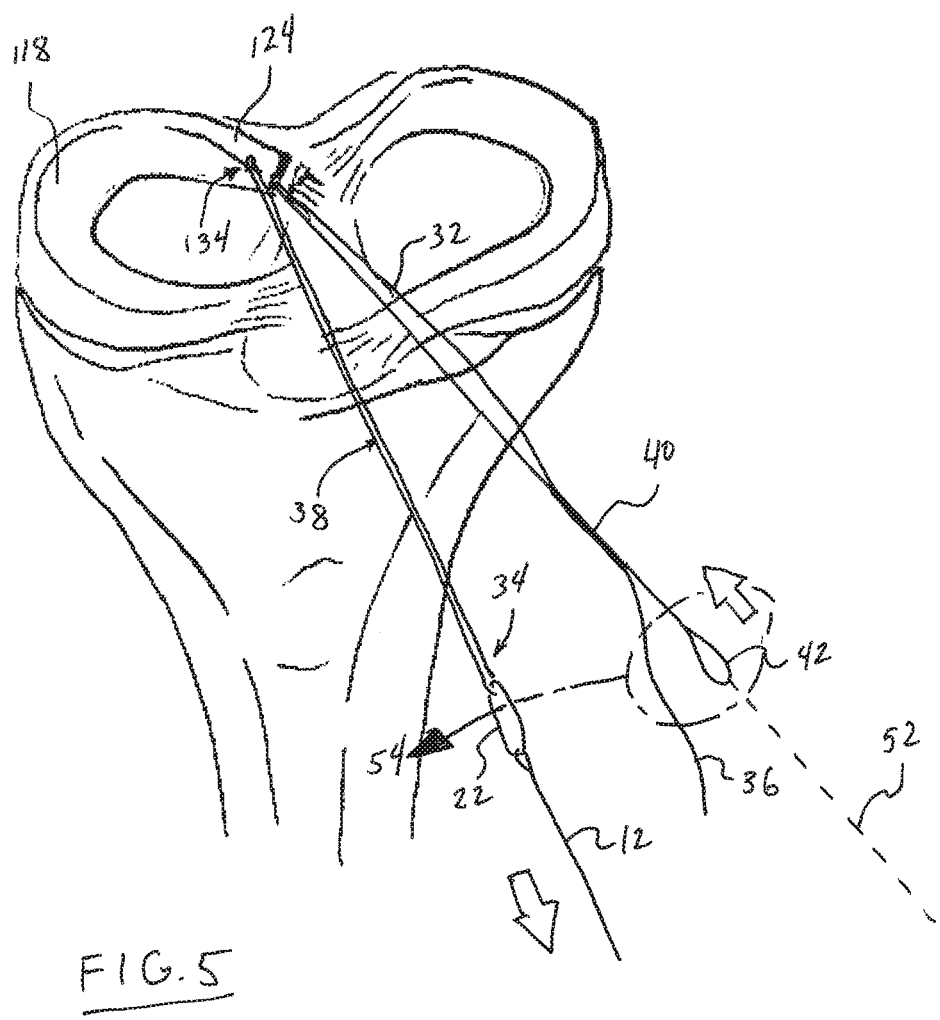
FIG. 5 illustrates a perspective view of an embodiment of a self-cinching suture construct positioned for installation on a torn meniscal root in a knee.

Referring now to FIG. 5, the suture construct device 10 is advanced further through hole passage 134 by pulling on shuttling suture 12 in a direction away from the passage hole 134 until continuous loop 22 has passed through passage hole 134. Additionally, as continuous loop 22 passes through passage hole 134, self-cinching suture member leading edge 34 on self-cinching suture member 32 is pulled through passage hole 134 and back away from the tissue. In the position shown in FIG. 5, two strands of self-cinching suture member 32 on the adjustable loop 38 region of self-cinching suture member 32 are partially passed through passage hole 134.

As shown in FIG. 5, the suture construct device 10 is now ready for a hitching step to connect the suture construct to the meniscal tissue. The self-cinching suture member fixed loop 42, sleeve 40, and the self-cinching suture member free end 36 may be passed together through continuous loop 22 in a pass-through direction 54, as shown in FIG. 5. In some embodiments, tether 52 is initially passed through the opening formed by continuous loop 22, and the tether 52 is pulled through first thereby also pulling through self-cinching suture member fixed loop 42, sleeve 40 and free end 36.

Figure 6:
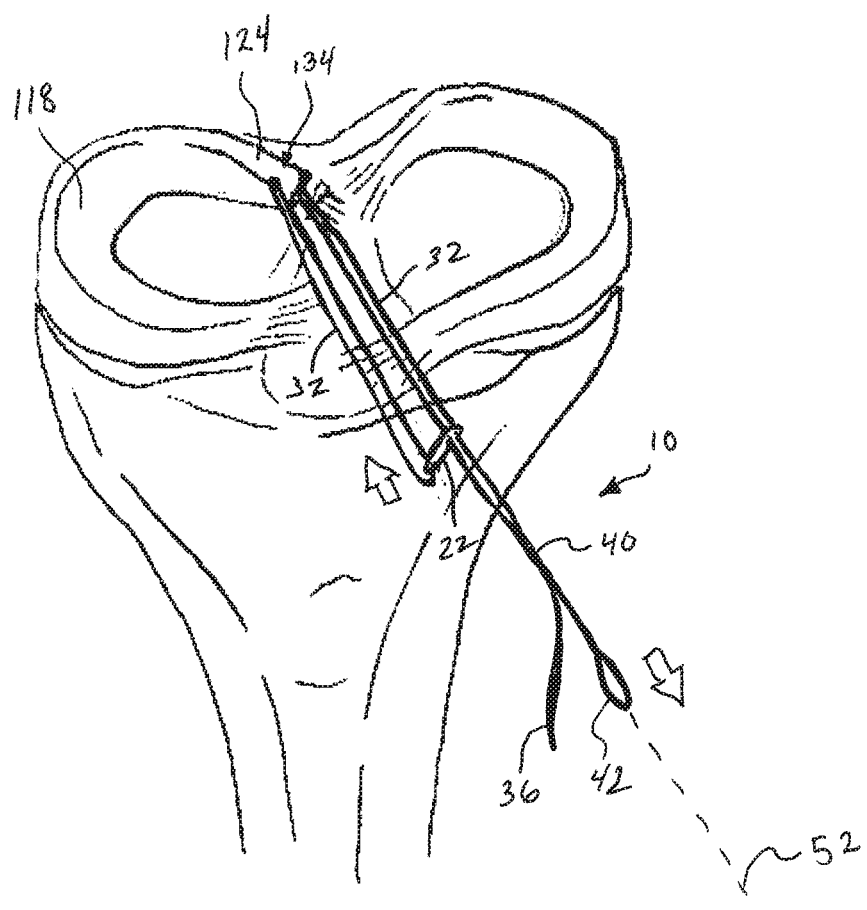
FIG. 6 illustrates a perspective view of an embodiment of a self-cinching suture construct positioned for installation on a torn meniscal root in a knee.

Referring to FIG. 6, once the self-cinching suture member fixed loop 42 and free end 36 are pulled through continuous loop 22, the shuttling suture 12 may be removed from the continuous loop 22. Shuttling suture may be cut to remove from continuous loop 22. After removal of shuttling suture 12, self-cinching suture member fixed loop 42, sleeve 40 and free end 36 may be pulled together in a direction away from the passage hole 134. This pulling motion causes continuous loop 22 to reverse direction and advance back toward passage hole 134. As continuous loop 22 advances back toward passage hole 134, sleeve 40 passes through continuous loop 22, and continuous loop 22 slides over two strands of self-cinching suture member 32 back toward passage hole 134.

Figure 7:
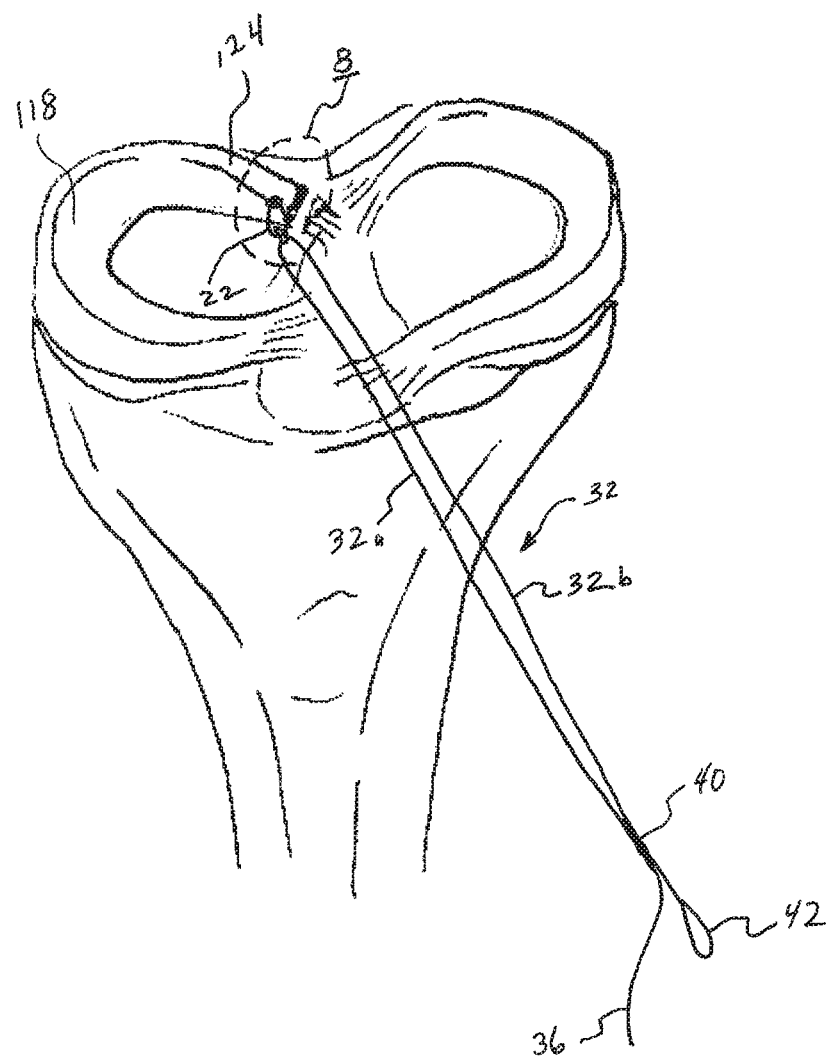
FIG. 7 illustrates a perspective view of an embodiment of a self-cinching suture construct positioned for installation on a torn meniscal root in a knee.
Figure 8:
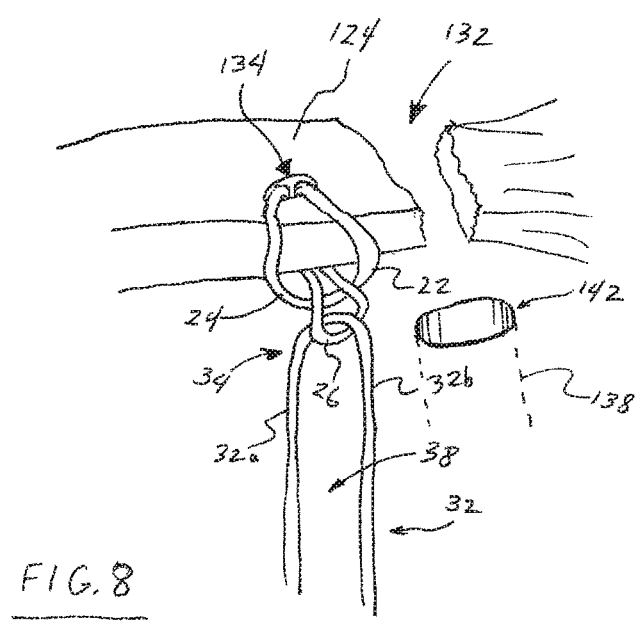
FIG. 8 illustrates a detail perspective view of an embodiment of a self-cinching suture construct positioned for installation on a torn meniscal root in a knee.

Referring to FIG. 7 and FIG. 8, when continuous loop 22 reaches passage hole 134, a portion of the trailing edge 26 on continuous loop 22 passes back through passage hole 134, forming a hitch on continuous loop 22 around the meniscus tissue adjacent root tear 132. In some embodiments, this causes a girth hitch on the meniscus tissue, as shown in FIG. 8. The self-cinching suture member leading edge 34 remains looped through continuous loop 22 as the girth hitch is formed, as seen in FIG. 8. In this configuration, a first strand 32a of self-cinching suture member 32 extends from one side of the continuous loop 22, and a second strand 32b of self-cinching suture member 32 extends from the other side of the continuous loop 22, as shown in FIG. 8. In this position, the suture construct device 10 is loosely secured to the meniscus tissue by a girth hitch.

By forming a girth hitch with two strands of continuous loop 22 passing through passage hole 134 as seen in FIG. 8, the chance of the suture cutting or slicing through the tissue is reduced as compared to suture constructs that provide a single strand passing through passage hole 134.

From the position shown in FIG. 8, first and second strands 32a, 32b on self-cinching suture member 32 form opposing sides of adjustable loop 38. Referring back to FIG. 7, suture construct device 10 includes a girth hitch formed by continuous loop 22 on the torn meniscus root tissue, and self-cinching suture member 32 is looped through the portion of continuous loop 22 extending from the girth hitch. As such, first and second strands 32a, 32b on self-cinching suture member 32 are positioned such that either strand may be pulled in one direction, causing a corresponding reverse motion on the other strand. For example, as seen in FIG. 7, first strand 32a extends away from the continuous loop 22 girth hitch toward sleeve 40. Self-cinching suture member free end 36 is formed on first strand 32a as first strand 32a passes through sleeve 40 on second strand 32b.

Notably, from the configuration shown in FIG. 8, when the suture construct is subsequently tightened, the first and second strands 32a, 32b slide through the hitched loop on continuous loop 22 and do not slide directly through passage hole 134. This prevents the first and second strands 32a, 32b from creating a slicing, or sawing, effect on the tissue itself as the suture construct is tightened.

Figure 9B:
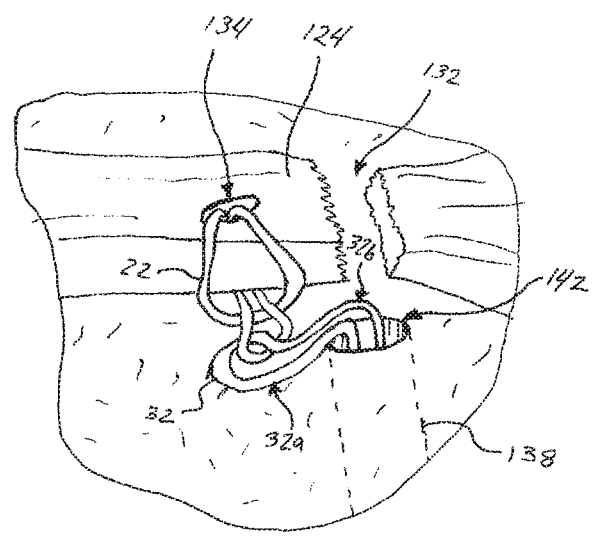
FIG. 9b illustrates a detail perspective view of an embodiment of a self-cinching suture construct positioned for installation on a torn meniscal root in a knee.

As seen in FIG. 8 and FIGS. 9a-9b, a transosseous tunnel 138 is drilled through the bone to provide a proximal tunnel opening 142 near the root meniscus tear location. The proximal tunnel opening 142 is laterally offset from the torn tissue flap in the medial direction away from the lateral meniscus in some embodiments. By offsetting the proximal tunnel opening 142 away from the torn tissue in a direction toward the tibial plateau, the tissue may be drawn tight laterally toward a proper anatomical position.

Tunnel 138 may be formed using any suitable instrument for drilling a transosseous tunnel in the bone tissue. After the continuous loop 22 girth hitch is formed on the meniscus tissue, an instrument such as a hook is inserted through tunnel 138 such that the end of the instrument protrudes from the proximal tunnel opening 142. The instrument is then used to grasp and pull the self-cinching suture member 32 through the tunnel 138 away from the continuous loop 22 girth hitch. This results in a configuration as shown in FIG. 9a and FIG. 9b where first and second strands 32a, 32b on self-cinching suture member 32 protrude from proximal tunnel opening 142 and loop through the hitched portion of the continuous loop 22 girth hitch. From this position, when the suture construct is tightened, first and second strands 32a, 32b will slide through the hitched loop in continuous loop 22 and not through the passage hole 134 in the tissue itself. This ability for the suture strands 32a, 32b to slide through the hitched loop on continuous loop 32 instead of the damaged tissue itself helps to prevent cutting or sawing of the tissue that could weaken the attachment.

Figure 14:
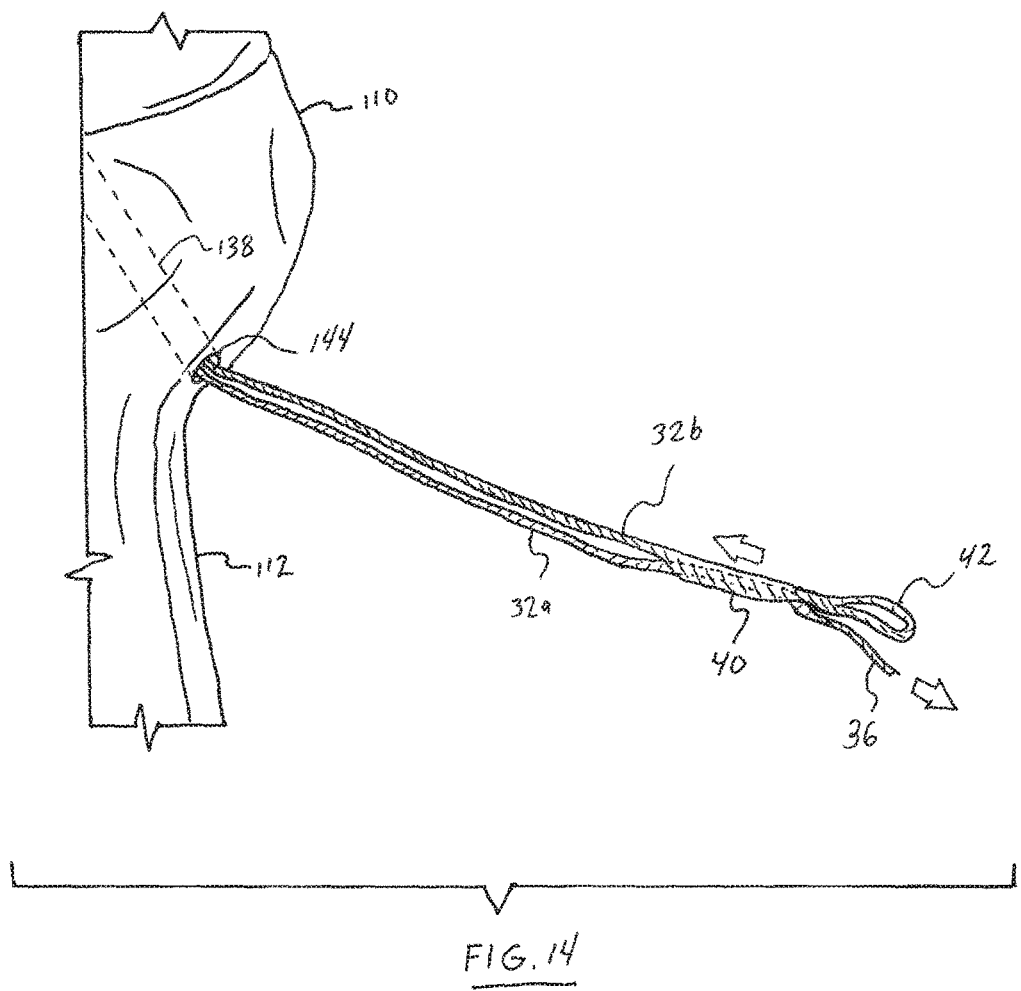
FIG. 14 illustrates a perspective view of an embodiment of a knee including a self-cinching suture construct device positioned for tensioning in accordance with the present disclosure.

As shown in FIG. 14, once the self-cinching suture member 32 is passed through tunnel 138, self-cinching suture member free end 36 may be pulled away from the bone, resulting in a sliding motion as the self-cinching suture member second strand 32b slides through continuous loop 22 girth hitch. The self-cinching suture member free end 36 slides through sleeve 40 easily until the suture is tensioned to a level where the sleeve tightens against the self-cinching suture member first strand 32a passing through sleeve 40 much like a finger-trap style device.

Figure 15:
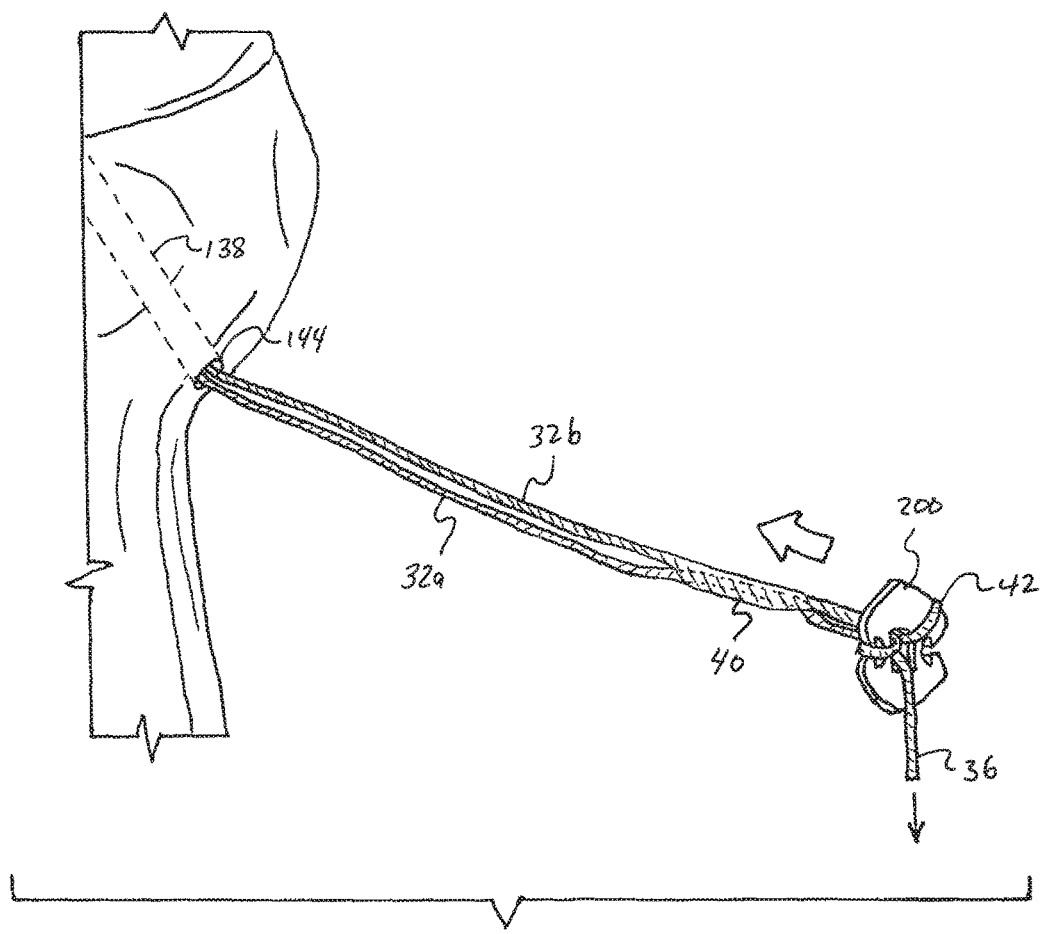
FIG. 15 illustrates a perspective view of an embodiment of a knee including a self-cinching suture construct device positioned for tensioning in accordance with the present disclosure.

In order to tension the suture construct device 10 to apply the appropriate traction against the torn meniscus root tissue, it is desirable to use a suture button, or suture anchor, on self-cinching suture member fixed loop 42 to pull tension against in some applications. For example, as shown in FIG. 15, a suture button 200 is positioned on self-cinching suture member fixed loop 42. The suture button 200 may include any suitable suture button or anchor known in the art. Once suture button 200 is installed, self-cinching suture member free end 36 may be pulled in tension away from the bone, resulting in sliding movement of the suture button 200 toward the distal tunnel opening 144.

Figure 16:
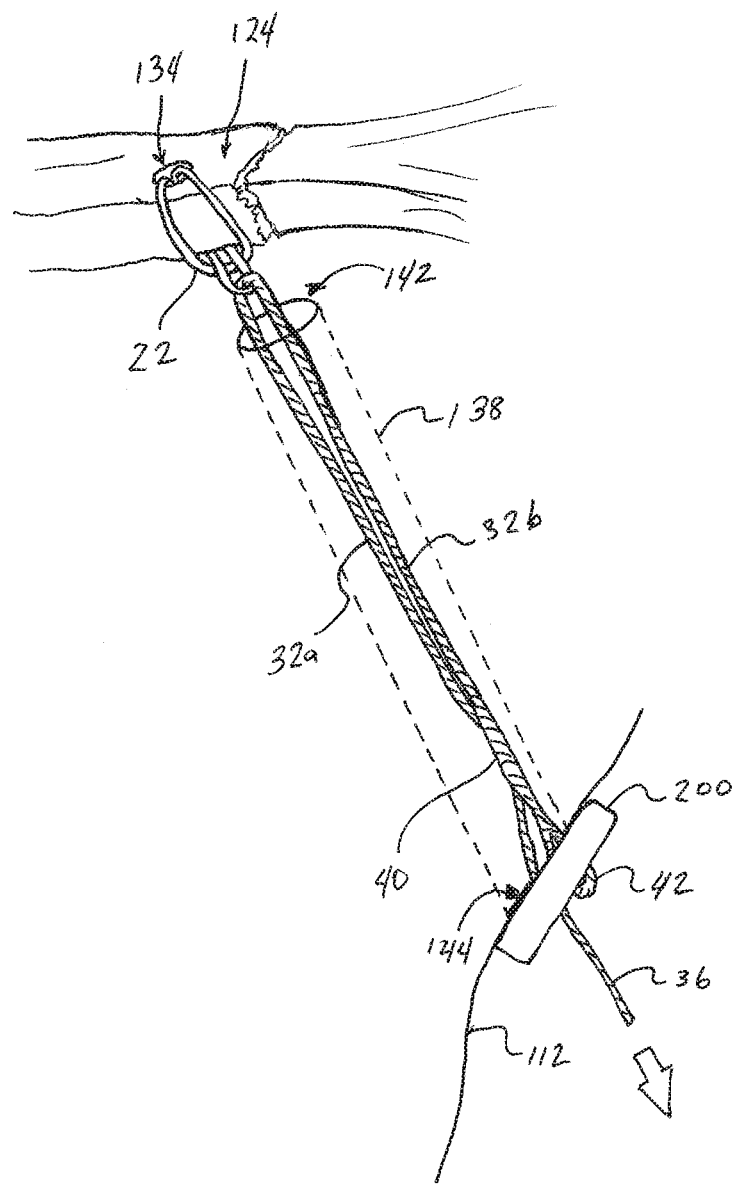
FIG. 16 illustrates a partial cross-sectional view of a knee showing an embodiment of a self-cinching suture construct device in a tensioned position.

As shown in FIG. 16, self-cinching suture member free end 36 is pulled away from distal tunnel opening 144 on bone 112 until suture button 200 is drawn against the distal tunnel opening 144 adjacent bone 112. In this position, sleeve 40 is housed inside the interior of tunnel 138, and first strand 32a passes through sleeve 40 at an axial position inside tunnel 138. As tension is drawn on self-cinching suture free end 36, sleeve 40 is drawn tighter against first strand 32a, preventing the first strand 32a from inadvertently slipping back toward the meniscus tissue.

The sleeve 40 is housed entirely inside tunnel 138 when suture button 200 contacts the bone 112 adjacent distal tunnel opening 144, thus preventing inadvertent wear or chafing on the sleeve 40 as self-cinching suture free end 36 is drawn tight. The resulting tension on suture construct device 10 pulls the torn meniscus root tissue toward its correct anatomical position near proximal tunnel opening 142. Additionally, the hitch formed on the meniscus root tissue helps prevent the suture material from tearing through the tissue and releasing the applied tension on the suture over time. Once the desired tension is applied, the self-cinching suture member free end 36 may be trimmed at the suture button 200. Multiple suture constructs may be installed through a single tunnel. Additionally, the self-cinching suture construct 10 of the present disclosure may be used combination with conventional knotted suture constructs in a single operation.

Figure 17:
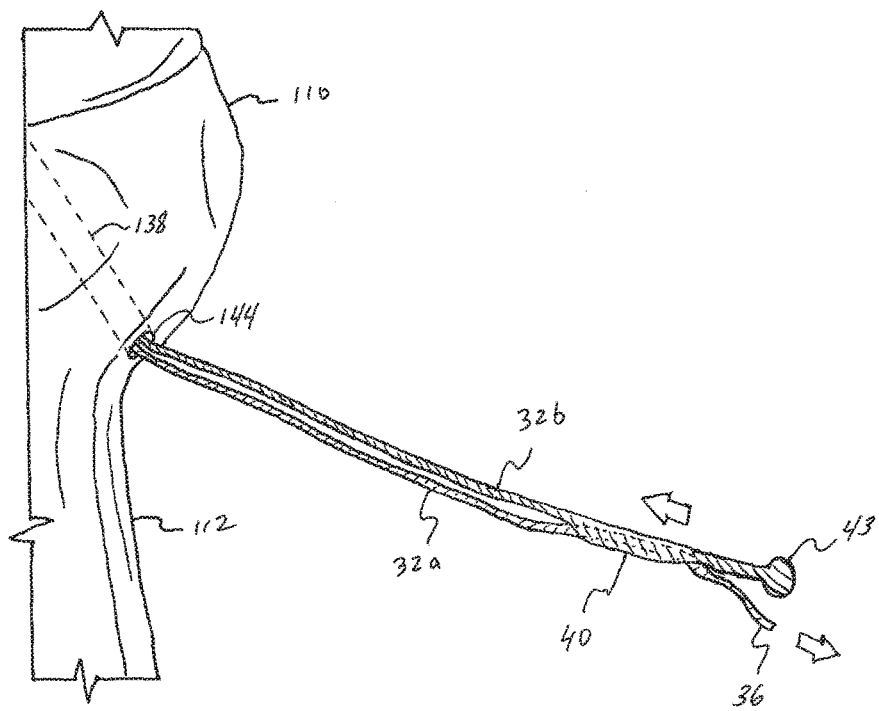
FIG. 17 illustrates a perspective view of an embodiment of a knee including a self-cinching suture construct device positioned for tensioning in accordance with the present disclosure.

Referring further to FIG. 17, in some embodiments self-cinching suture member 32 includes any suitable detent structure 43 suitable to prevent second strand 32b from being pulled back through tunnel 138. Detent structure 43 may engage a suture button 200 or may alternatively press directly against the bone adjacent distal tunnel opening 144. For example, in some embodiments, detent structure 43 forms a fixed loop as discussed above that may be positioned around a suture button in a hitch or loop to secure one end of the self-cinching suture member 32 to the suture button 200. However, in other embodiments, detent structure 43 may include any type of suitable cable stop or tension member terminal end dimensioned to engage a corresponding slot, recess or structure on suture button 200 to secure one end of the self-cinching suture member 32 to the suture button 200 or alternatively dimensioned to prevent the second strand 32 from advancing back into the tunnel 138.

Numerous other configurations for the suture construct device of the present disclosure may be realized when in use. The disclosed embodiments and configurations of the suture construct device are presented only as examples, and are not intended to illustrate all possible embodiments and configurations for the apparatus.

Thus, although there have been described particular embodiments of the present invention of a new and useful suture construct device, it is not intended that such references be construed as limitations upon the scope of this invention except as set forth in the following claims.

What is claimed is:

1. A suture construct apparatus, comprising:
    a shuttling suture having a shuttling suture leading end and a shuttling suture trailing end;
    a shuttling suture fixed loop formed on the shuttling suture trailing end;
    a continuous loop member disposed on the shuttling suture fixed loop; and
    a self-cinching suture member disposed on the continuous loop member, the self-cinching suture member including a first strand, a second strand and a sleeve defined on the second strand,
    wherein the first strand passes through the sleeve and forms a self-cinching suture member free end, and
    wherein the first strand is axially moveable through the sleeve.

2. The apparatus of claim 1, further comprising a self-cinching suture member fixed loop formed on the second strand.

3. The apparatus of claim 2, wherein the sleeve of the self-cinching suture member is operable to tighten against the first strand when tension is applied to the self-cinching suture member free end.

4. The apparatus of claim 1, wherein the first and second strands form an adjustable loop.

5. The apparatus of claim 4, wherein the length of the adjustable loop is adjustable by sliding the first strand through the sleeve.

6. The apparatus of claim 5, wherein the sleeve of the self-cinching suture member is operable to tighten against the first strand when tension is applied to the self-cinching suture member free end.

7. The apparatus of claim 1, further comprising a suture button disposed on the self-cinching suture member fixed loop.

8. The apparatus of claim 7, wherein the sleeve of the self-cinching suture member is operable to tighten against the first strand when tension is applied to the self-cinching suture member free end.

9. The apparatus of claim 1, further comprising a girth hitch formed on the continuous loop.

10. The apparatus of claim 9, wherein the sleeve of the self-cinching suture member is operable to tighten against the first strand when tension is applied to the self-cinching suture member free end.

11. The apparatus of claim 1, wherein the shuttling suture includes a first section having a first shuttling suture diameter and a second section having a second shuttling suture diameter, wherein the second shuttling suture diameter is greater than the first shuttling suture diameter.

12. The apparatus of claim 11, wherein the sleeve of the self-cinching suture member is operable to tighten against the first strand when tension is applied to the self-cinching suture member free end.

13. The apparatus of claim 1, further comprising a dilation member disposed on the shuttling suture.

14. The apparatus of claim 13, wherein the sleeve of the self-cinching suture member is operable to tighten against the first strand when tension is applied to the self-cinching suture member free end.

15. The apparatus of claim 14, wherein the dilation member is integrally formed on the shuttling suture.

16. A suture construct apparatus for repairing meniscus tissue in a knee, comprising:
    a shuttling suture including a leading shuttling suture free end configured for insertion through a passage hole in the meniscus and a trailing end opposite the leading shuttling suture free end;
    a shuttling suture fixed loop disposed on the trailing end of the shuttling suture opposite the leading shuttling suture free end;
    a continuous loop forming a ring-shaped opening, the continuous loop passing through the shuttling suture fixed loop;
    a self-cinching suture member passing through the ring-shaped opening of the continuous loop, the self-cinching suture member including a first strand and a second strand each extending from the continuous loop suture opposite the shuttling suture, the first strand forming a self-cinching suture member free end; and
    a self-cinching sleeve defined on the second strand, wherein the first strand passes through the sleeve.

17. The apparatus of claim 16, further comprising a detent structure disposed on the second strand.

18. The apparatus of claim 17, wherein the detent structure is a fixed loop on the second strand.

19. The apparatus of claim 16, wherein the self-cinching sleeve is operable to tighten against the first strand when tension is applied to the self-cinching suture member.

20. The apparatus of claim 19, further comprising the continuous loop configured to form a girth hitch around the meniscus tissue.

* * * * *